United States Patent [19]

Harigaya et al.

[11] Patent Number: 4,661,630
[45] Date of Patent: Apr. 28, 1987

[54] CARBOXYLIC ACID AMIDES AND THEIR DERIVATIVES

[75] Inventors: Yasuji Harigaya, Chiba; Hiroo Ogura; Mitsuo Mihara, both of Ibaraki; Motosuke Yamanaka, Chiba; Kiyomi Yamatsu, Kanagawa, all of Japan

[73] Assignee: Eisai Co., Ltd., Tokyo, Japan

[21] Appl. No.: 803,526

[22] Filed: Dec. 2, 1985

Related U.S. Application Data

[63] Continuation of Ser. No. 563,924, Dec. 21, 1983, abandoned.

[30] Foreign Application Priority Data

Dec. 27, 1982 [JP] Japan .................. 57-226685

[51] Int. Cl.$^4$ ........................................ C07C 103/737
[52] U.S. Cl. .................... 562/455; 548/476; 548/513; 548/435; 549/237; 549/240
[58] Field of Search .............. 514/398, 621; 71/118; 562/455, 457; 548/476, 513, 435; 549/237, 240

[56] References Cited

U.S. PATENT DOCUMENTS

| | | | |
|---|---|---|---|
| 2,794,811 | 6/1957 | Winstrom | 549/240 |
| 2,959,599 | 11/1960 | Bailey | 549/240 |
| 3,085,096 | 4/1963 | Kerr et al. | 549/240 |
| 3,507,904 | 4/1970 | Schwartz et al. | 562/457 |
| 3,549,655 | 12/1970 | Bublitz | 549/240 |
| 3,654,302 | 4/1972 | Schwartz et al. | 548/513 |
| 3,658,892 | 4/1972 | Martin et al. | 562/455 |
| 3,745,170 | 7/1973 | Fujinami et al. | 548/513 |
| 3,825,594 | 7/1974 | Houlihan | 424/324 |
| 3,987,056 | 10/1976 | Cobb | 548/513 |
| 4,002,460 | 1/1977 | Pallos | 562/442 |
| 4,025,505 | 5/1977 | Gschwend et al. | 548/476 |
| 4,132,716 | 1/1979 | Kvita et al. | 548/513 |
| 4,361,576 | 11/1982 | Buhler et al. | 548/513 |
| 4,409,018 | 10/1983 | Ishida | 548/513 |
| 4,596,826 | 6/1986 | Harigaya et al. | 562/455 |

FOREIGN PATENT DOCUMENTS

| | | |
|---|---|---|
| 2369252 | 6/1978 | France . |
| 41-7075 | 4/1966 | Japan . |
| 55-24127 | 2/1980 | Japan . |

OTHER PUBLICATIONS

Burger et al—J. Organic Chemistry—18, 192-195 (1953).

*Primary Examiner*—Veronica P. Hoke
*Attorney, Agent, or Firm*—Wenderoth, Lind & Ponack

[57] ABSTRACT

Described herein are novel carboxylic acid amide compounds or carboximide compounds represented by the general formula:

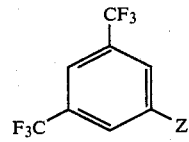

wherein Z represents either the monoamido radical of an aromatic or cycloaliphatic ortho dicarboxylic acid or the amide of the corresponding anhydride, and their pharmaceutically acceptable salts; processes for the production thereof; and medicines containing the same. The novel compounds are useful as treating, preventing and improving agents for diseases attended with cerebral dysfunction as well as various symptoms caused by the said diseases.

10 Claims, No Drawings

CARBOXYLIC ACID AMIDES AND THEIR DERIVATIVES

This application is a continuation of now abandoned application Ser. No. 563,924, filed Dec. 21, 1983.

The present invention relates to novel carboxylic acid amide compounds or carboximide compounds, to processes for their production and to medicines containing the same.

More particularly, this invention relates to carboxylic acid amide compounds or carboximide compounds represented by the general formula:-

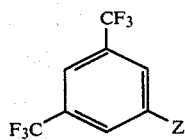

and the salts thereof;
wherein Z represents a group of the formula:

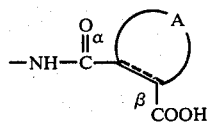 (1)

or
a group of the formula:

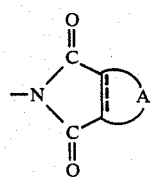 (2)

wherein A constitutes along with two carbon atoms respectively represented by α and β, a group of the formula:

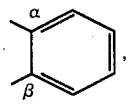, a group of the formula:

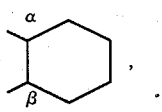, a group of the formula:

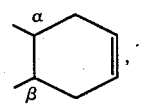, a group of the formula:

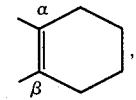, a group of the formula:

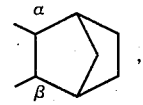, a group of the formula:

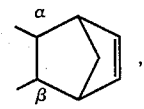, a group of the formula:

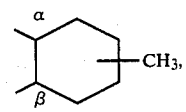, or a group of the formula:

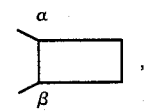, and ====== denotes a single bond or a double bond; and relates to processes for their production; and to medicines containing the same.

In the definition of A in the general formula (I) above, where A represents a group of the formula:

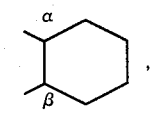, a group of the formula:

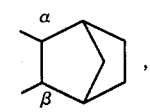, a group of the formula:

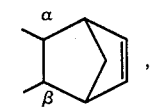, or a group of the formula:

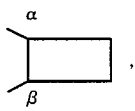

these groups may exist in stereoisomeric forms, and often exist as exo and endo forms, and cis and trans forms, and therefore, the present invention encompasses all such stereoisomers.

The salts of the compounds according to the present invention include Na, K, Ca, and Mg salts, for example.

The carboxylic acid amide compounds provided by the present invention are novel compounds which have not yet been disclosed in any literature, and it has now been discovered that these compounds have excellent anti-convulsant, anti-hypoxic, anti-anxiety and sedative activities, and therefore, are useful as treating, preventing and improving agents for diseases attended with cerebral dysfunction such as epilepsy, cerebrovascular disease sequelae, head injury sequelae, and the like. In addition, these compounds are useful as treating, preventing and improving agents for various symptoms caused by diseases, which are attended with cerebral dysfunction such as epilepsy, cerebrovascular diseases sequelae, head injury sequelae and the like, the said symptoms including convulsion, disturbance of consciousness, impaired memory or disturbance of movement. Further, the compounds according to the present invention also have anti-ulcer, anti-asthmatic, hypo-cholesterol and anti-inflammatory activities, and therefore, are also useful as anti-ulcer, anti-asthematic, hypo-cholesterol and anti-inflammatory drugs. The present inventors have discovered that these compounds unexpectedly have the above-mentioned excellent activities, and have thus accomplished the present invention.

It is therefore an object of the present invention to provide novel compounds which are useful as medicines such as treating, preventing and improving agents for diseases attended with cerebral dysfunction such as epilepsy, cerebrovascular diseases sequelae, head injury sequelae, and the like; and useful as medicines such as treating, preventing and improving agents for various symptoms caused by diseases, which are attended with cerebral dysfunction such as epilepsy, cerebrovascular disease sequelae, head injury sequelae and the like, the said symptoms including convulsion, disturbance of consciousness, impaired memory or disturbance of movement; and further as medicines such as anti-ulcer, anti-asthmatic, hypo-cholesterol and anti-inflammatory drugs.

It is an another object of the present invention to provide processes for the production of novel compounds useful as such medicines.

It is a further object of the present invention to provide novel treating, preventing and improving agents for diseases attended with cerebral dysfunction such as epilepsy, cerebrovascular disease sequelae, head injury sequelae and the like; treating, preventing and improving agents for various symptoms caused by diseases, which are attended with cerebral dysfunction such as epilepsy, cerebrovascular diseases sequelae, head injury sequelae and the like, the said symptoms including convulsion, disturbance of consciousness, impaired memory or disturbance of movement; and medicines including anti-ulcer, anti-asthmatic, hypo-cholesterol and anti-inflammatory drugs.

The compounds (I) of the present invention can be produced by various routes, among which some representive examples commonly employed are described below:

(1) Where Z in the formula (I) represents a group of the formula:

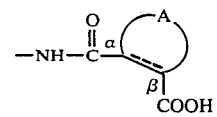

wherein A is as defined above,

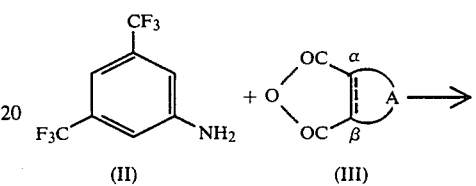

that is, 3,5-bistrifluoromethyl aniline of the formula (II) is reacted with a carboxylic anhydride of the formula (III) in a conventional manner to provide a desired compound (I). In this case, the reaction is conducted under a heating condition, usually at room temperature or a temperature of about 150° C. or less, and in a solvent such as, for example, benzene, chloroform, toluene, isopropyl ether, and acetonitrile.

(2) Where Z in the formula (I) represents a group of the formula:

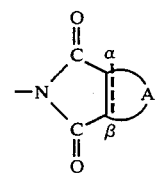

the carboxylic acid amide (IV),

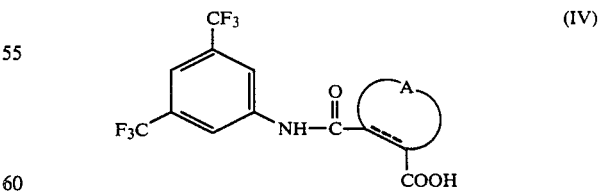

for example, produced in the process (1), is dehydrated by heating to a temperature of 180° to 220° C. in the absence of solvent, or refluxed with thionyl chloride added thereto for a several time in a non-protonic solvent such as benzen and toluene. After the completion of reaction, the soluvent is evaporated off to provide a crude imide compound.

Alternatively, the carboxylic anhydride employed in the process (I) is added in an equimolar amount to 3,5-bistrifluoromethyl aniline, and the resulting compound is then dehydrated by heating to a temperature of about 180° to 220° C. in the absence of solvent.

(3) Where the carboxylic acid amide compound of the present invention, obtained in the process (1) or (2), is in the cis form, the conversion of this compound into the compound in the trans form can be established by the following process.

That is, the corresponding cis-form compound is reacted at a temperature of 50° to 100° C. for 5 to 10 times in an alkali aqueous solution such as NaOH and KOH and then neutralized with a dilute mineral acid, followed by extraction with a suitable organic solvent. The extracted material is dried, and the solvent is evaporated off to provide a trans-form compound.

Representative compounds of the present invention are illustrated below, but it should be understood that the present invention is not restricted thereto.

Cis-2-[(3,5-bistrifluoromethyl phenyl)-aminocarbonyl]-cyclohexane carboxylic acid
Trans-2-[(3,5-bistrifluoromethyl phenyl)-aminocarbonyl]-cyclohexane carboxylic acid
Cis-6-[(3,5-bistrifluoromethyl phenyl)-aminocarbonyl]-3-cyclohexene carboxylic acid
2-[(3,5-bistrifluoromethyl phenyl)-aminocarbonyl]-1-cyclohexene carboxylic acid
2-[(3,5-bistrifluoromethyl phenyl)-aminocarbonyl]-benzoic acid
Cis-2-[(3,5-bistrifluoromethyl phenyl)-aminocarbonyl]-cyclobutane carboxylic acid
Trans-2-[(3,5-bistrifluoromethyl phenyl)-aminocarbonyl]-cyclobutane carboxylic acid
Cis-endo-3-[(3,5-bistrifluoromethyl phenyl)-aminocarbonyl]-5-bicyclo-(2,2,1)-heptene-2-carboxylic acid
Trans-3-[(3,5-bistrifluoromethyl phenyl)-aminocarbonyl]-5-bicyclo-(2,2,1)-heptene-2-carboxylic acid
Cis-endo-3-[(3,5-bistrifluoromethyl phenyl)-aminocarbonyl]-bicyclo-(2,2,1)-heptane-2-carboxylic acid
Trans-3-[(3,5-bistrifluoromethyl phenyl)-aminocarbonyl]-bicyclo-(2,2,1)-heptane-2-carboxylic acid
Cis-2-[(3,5-bistrifluoromethyl phenyl)-aminocarbonyl]-4(5)-methyl-cyclohexane carboxylic acid
Cis-2-[(3,5-bistrifluoromethyl phenyl)-aminocarbonyl]-4(5)-methyl-cyclohexane carboxylic acid
N-(3,5-bistrifluoromethyl phenyl)-cis-cyclohexane-1,2-dicarboximide
N-(3,5-bistrifluoromethyl phenyl)-4-cyclohexene-1,2-dicarboximide
N-(3,5-bistrifluoromethyl phenyl)-1-cyclohexane-1,2-dicarboximide
N-(3,5-bistrifluoromethyl phenyl)-trans-cyclohexane-1,2-dicarboximide
N-(3,5-bistrifluoromethyl phenyl)-cis-endo-bicyclo-(2,2,1)-heptane-2,3-dicarboximide
N-(3,5-bistrifluoromethyl phenyl)-cis-endo-5-bicyclo-(2,2,1)-heptene-2,3-dicarboximide
N-(3,5-bistrifluoromethyl phenyl)-cis-cyclobutane-1,2-dicarboximide
N-(3,5-bistrifluoromethyl phenyl)-phthalimide
N-(3,5-bistrifluoromethyl phenyl)-4(5)-methyl-cyclohexane-1,2-dicarboximide In order to explain in more detail, the effects of the compounds according to the present invention, experimental examples will be given below.

EXPERIMENT (1) Anti-electroshock convulsion activity

The effects of the representative compounds of the present invention on maximal electroshock seizures in mice were determined by the method of Goodman et al. [Goodman L. S., Singh Grewal M., Brown W. C. and Swinyard E. A., J. Pharmacol, Exp. Ther., 108, 168–176 (1953)]. At 2 hours after oral administration of test compounds, current (25 mA, 0.25 sec.) was delivered to animals with an electroshock device (made by Unique Medical). The results are shown in Table 1.

TEST COMPOUNDS

Compound A: cis-2-[(3,5-bistrifluoromethyl)-phenyl-aminocarbonyl]-cyclohexane carboxylic acid (Example 1)

Compound B: trans-2-[(3,5-bistrifluoromethyl)-phenyl-aminocarbonyl]-cyclohexane carboxylic acid (Example 2)

Compound C: cis-6-[(3,5-bistrifluoromethyl-phenyl)-aminocarbonyl]-3-cyclohexene carboxylic acid (Example 3)

Compound D: 2-[(3,5-bistrifluoromethyl-phenyl)-aminocarbonyl]-1-cyclohexene carboxylic acid (Example 4)

Compound E: cis-endo-3-[(3,5-bistrifluoromethyl-phenyl)-aminocarbonyl]-bicyclo-(2,2,1)-heptane-2-carboxylic acid (Example 10)

Compound F: cis-2-[(3,5-bistrifluoromethyl-phenyl)-aminocarbonyl]-4(5)-methyl-cyclohexane carboxylic acid (Example 12)

Compound G: N-(3,5-bistrifluoromethyl phenyl)-cyclohexane-1,2-dicarboximide

Compound H: N-(3,5-bistrifluoromethyl phenyl)-4-cyclohexene-1,2-dicarboximide

TABLE 1

| Anti-electroshock convulsion activity | | | | | |
|---|---|---|---|---|---|
| Inhibition (%) of tonic extension (n = 8) Dosage (mg/kg p.o.) | | | | | |
| Test Compound | 320 | 80 | 40 | 20 | 10 |
| Compound A | 100 | 100 | 100 | 50 | 25 |
| Compound B | 100 | 0 | | | |
| Compound C | 100 | 100 | 100 | 100 | 12.5 |
| Compound D | 100 | 0 | | | |
| Compound E | 100 | 0 | | | |
| Compound F | 100 | 100 | 50 | | |
| Compound G | 100 | 100 | 25 | | |
| Compound H | 87.5 | 50 | | | |

(2) Anti-metrazol activity, Anti-hypoxic activity and acute toxicity (a) Anti-metrazol activity of the compounds of the present invention was examined in male STD-ddY mice. Both Compound A and Compound C, representative compounds among the compounds according to the present invention, in oral doses of 20 to 80 mg/kg, showed a dose-dependent antagonism against metrazol-induced convulsive death.

(b) Antagonistic activity of the compounds against the mortality induced by potassium cyanide was examined in male STD-ddY mice. The Compound A as well as Compound C exhibited a potent anti-hypoxic activity with a dose range of 10 to 20 mg/kg, p.o.

(c) Acute toxicity of the compounds of the present invention was relatively low. Oral $LD_{50}$ values of Compound A and Compound C in mice ranged from 1000 to 2000 mg/kg.

As in the above results, the compounds of the present invention have excellent anti-convulsant and anti-hypoxic activities, and can also be anticipated to have tranquilizing activity. It can therefore be understood that they are obviously useful as treating, preventing and improving agents for diseases attended with cerebral dysfunction such as eqilepsy, cerebrovascular disease sequelae and head injury sequelae, and the like.

The compounds of the present invention are those having a lower toxicity and a high safety, and hence, can be administered continuously for a long period. Even in this sense, the present invention is high in utility value.

In administering the compounds of the present invention into patients of the above-mentioned diseases, although the dosage varies widely, depending on the kind of disease, the severity of the condition of patient, the type of compound and the age of patient, but it may be in the range of about 10 mg to 1,000 mg, preferably about 50 mg to 300 mg, per day for a human adult in oral or parenteral administration. Tor preparations of the compounds of the present invention, they may be made in the form of, for example, powders, granules, particulates, tablets, capsules and injectable compositions, using usual carrier, in accordance with conventional pharmaceutical practice.

More specifically, for preparing oral solid preparations, the main drug is mixed with an excipient and further, if necessary, a binder, disintegrator, lubricants, colorants, flavoring agent, etc., and then formed into tablets, coated tablets, particulates, powders, capsules, etc., in conventional manner.

As the excipients, there can be used, for example, lactose, corn starch, white sugar, glucose, sorbitol, crystalline cellulose, silicon dioxide, etc.. As the binders, there can be used, for example, polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone, etc.. As the disintegrators, there can be used, for example, starch, agar, gelatin powder, crystalline cellulose, calcium carbonate, sodium bicarbonate, calcium citrate, dextrin, pectin, etc.. As the lubricants, there can be used, for example, magnesium stearate, talc, polyethylene glycol, silica, hardened vegetable oils, etc.. As the colorants, there can be used those allowed as additives to medicines. As the flavoring agents, there can be used cocoa powders, menthol, aromatic acids, mint oil, camphol, cinnamon powder, etc.. These tablets, particulates etc. may of course be suitably coated with sugar, gelatin or the like, if necessary.

For preparing an injectable solution, the main drug is mixed with a pH adjusting agent, buffer, stabilizer, solubilizing agent, etc., if necessary and made into compositions for subcutaneous, intramuscular, intravenous injections etc. in the conventional manner.

A preparation example is given below which contains, as an active ingredient, cis-2-[(3,5-bistrifluoromethyl phenyl)-aminocarbonyl]-cyclohexane carboxylic acid (which will be referred as to a main drug hereinafter) which is a representative compound of the compounds according to the present invention.

| Preparation Example (tablet) | |
|---|---|
| Main drug | 10 g |
| Crystalline cellulose | 90 g |
| Corn starch | 66 g |
| Hydroxypropyl cellulose | 10 g |
| Magnesium stearate | 4 g |

The mixture consisting of the above components was formed into tablets (each weighing 180 mg) in the conventional manner by the above-mentioned prescription.

The present invention is further illustrated by way of the following examples, which are on no account intended to limit the present invention.

EXAMPLE 1

Cis-2-[(3,5-bistrifluoromethyl phenyl)-aminocarbonyl]-cyclohexane carboxylic acid A mixture of 2.3 g (0.01 mole) of 3,5-bistrifluoromethyl aniline and 1.5 g (0.01 mole) of cis-cyclohexane-1,2-dicarboxylic anhydride was stirred in iso-propyl ether at room temperature. The precipitated crystals were filtered off to give 3.0 g of the title compound.

Yield: 80%, Melting point: 169°–170° C. (decomposition)

Elemental analysis: for $C_{16}H_{15}NO_3F_6$

|  | C | H | N |
|---|---|---|---|
| Calculated (%): | 50.26 | 3.70 | 3.66 |
| Found (%): | 50.27 | 3.92 | 3.63 |

EXAMPLE 2

Trans-2-[(3,5-bistrifluoromethyl phenyl)-aminocarbonyl]-cyclohexane carboxylic acid Using, as starting materials, 2.3 g of 3,5-bistrifluoromethyl aniline, and 1.5 g (0.01 mole) of trans-cyclohexane-1,2-dicarboxylic anhydride, the title compound was obtained in the same manner as in Example 1.

Melting point: 177°–179° C.

Elemental analysis: for $C_{16}H_{15}NO_3F_6$

|  | C | H | N |
|---|---|---|---|
| Calculated (%): | 50.26 | 3.70 | 3.66 |
| Found (%): | 50.36 | 4.01 | 3.52 |

EXAMPLE 3

Cis-6-[(3,5-bistrifluoromethyl phenyl)-aminocarbonyl]-3-cyclohexene carboxylic acid Using as starting materials, 2.3 g of 3,5-bistrifluoromethyl aniline and 1.5 g of 4-cyclohexene dicarboxylic anhydride, the title compound was obtained in the same manner as in Example 1.

Melting point: 166°–167° C.

Elemental analysis: for $C_{16}H_{13}NO_3F_6$

|  | C | H | N |
|---|---|---|---|
| Calculated (%): | 50.40 | 3.44 | 3.67 |
| Found (%): | 50.48 | 3.42 | 3.59 |

EXAMPLE 4

2-[(3,5-bistrifluoromethyl phenyl)-aminocarbonyl]-1-cyclohexene carboxylic acid

Using as starting materials, 2.3 g of 3,5-bistrifluoromethyl aniline and 1.5 g of 1-cyclohexene-1,2-dicarboxylic anhydride, the title compound was obtained in the same manner as in Example 1.

Melting point: 112°–114° C.
Elemental analysis: for $C_{16}H_{13}NO_3F_6$

|  | C | H | N |
|---|---|---|---|
| Calculated (%): | 50.39 | 3.44 | 3.67 |
| Found (%): | 50.29 | 3.39 | 3.60 |

EXAMPLE 5

2-[(3,5-bistrifluoromethyl phenyl)-aminocarbonyl]-benzoic acid

From 2.3 g of 3,5-bistrifluoromethyl aniline and 1.5 g of phthalic anhydride used as starting materials, the title compound was obtained in the same manner as in Example 1.

Melting poaint: 186° C. (decomposition)
Elemental analysis: for $C_{16}N_9NO_3F_6$

|  | C | H | N |
|---|---|---|---|
| Calculated (%): | 51.05 | 2.39 | 3.66 |
| Found (%): | 50.93 | 2.40 | 3.71 |

EXAMPLE 6

Cis-2-[(3,5-bistrifluoromethyl phenyl)-aminocarbonyl]-cyclobutane carboxylic acid From 2.3 g of 3,5-bistrifluoromethyl aniline and 1.1 g of cyclobutane-1,2-dicarboxylic anhydride used as starting materials, the title compound was obtained in the same manner as in Example 1.

Melting point: 217° C. (decomposition)
Elemental analysis: for $C_{14}H_{11}NO_3F_6$

|  | C | H | N |
|---|---|---|---|
| Calculated (%): | 47.32 | 3.12 | 3.94 |
| Found (%): | 47.10 | 3.05 | 3.84 |

EXAMPLE 7

Trans-2-[(3,5-bistrifluoromethyl phenyl)-aminocarbonyl]-cyclobutane carboxylic acid 5.0 g of cis-2-[(3,5-bistrifluoromethyl phenyl)-aminocarbonyl]-cyclobutane carboxylic acid was reacted at a temperature of 50° C. for three hours in 10% aqueous caustic soda solution. The products were neutralized with dilute hydrochloric acid, extracted with ethyl acetate and then recrystallized from acetonitrile to give 3.4 g of the title compounds (yield: 68%).

Melting point: 170°–171° C.
Elemental analysis: for $C_{14}H_{11}NO_3F_6$

|  | C | H | N |
|---|---|---|---|
| Calculated (%): | 47.32 | 3.12 | 3.94 |
| Found (%): | 47.36 | 3.14 | 3.92 |

EXAMPLE 8

Cis-endo-3-[(3,5-bistrifluoromethyl phenyl)-aminocarbonyl]-5-bicyclo-(2,2,1)-heptene-2-carboxylic acid Starting from 2.3 g of 3,5-bistrifluoromethyl aniline and 1.6 g of cis-endo-5-norbornene-2,3-carboxylic anhydride, the title compound was obtained in the same manner as in Example 1.

Melting point: 169.5°–171° C.
Elemental analysis: for $C_{17}H_{13}NO_3F_6$

|  | C | H | N |
|---|---|---|---|
| Calculated (%): | 51.91 | 3.34 | 3.56 |
| Found (%): | 52.18 | 3.33 | 3.56 |

EXAMPLE 9

Trans-3-[(3,5-bistrifluoromethyl phenyl)-aminocarbonyl]-5'-bicyclo-(2,2,1)-heptene-2-carboxylic acid 4.5 g of cis-endo-3-[(3,5-bistrifluoromethyl phenyl)-aminocarbonyl]-5-bicyclo-(2,2,1)-heptene-2-carboxylic acid was reacted at a temperature of 80° C. for two hours in 5% aqueous caustic soda solution. The products were neutralized with dilute hydrochloric acid, extracted with ethyl acetate and recrystallized from acetonitrile to give 2.2 g of the title compound.

Melting point: 212°–213° C.
Elemental analysis: for $C_{17}H_{13}NO_3F_6$

|  | C | H | N |
|---|---|---|---|
| Calculated (%): | 51.91 | 3.34 | 3.56 |
| Found (%): | 51.93 | 3.30 | 3.60 |

EXAMPLE 10

Cis-endo-3-[(3,5-bistrifluoromethyl phenyl)-aminocarbonyl]-bicyclo-(2,2,1)-heptane-2-carboxylic acid Starting from 2.3 g of 3,5-bistrifluoromethyl aniline and 1.6 g of cis-endo-bicyclo-(2,2,1)-heptane dicarboxylic anhydride, the title compound was obtained in the same manner as in Example 1.

Melting point: 169°–170° C.
Elemental analysis: for $C_{17}H_{13}NO_3F_6$

|  | C | H | N |
|---|---|---|---|
| Calculated (%): | 51.91 | 3.34 | 3.56 |
| Found (%): | 51.93 | 3.30 | 3.60 |

EXAMPLE 11

Trans-3-[(3,5-bistrifluoromethyl phenyl)-aminocarbonyl]-bicyclo-(2,2,1)-heptane-2-carboxylic acid Starting from 2.3 g of 3,5-bistrifluoromethyl aniline and 3.5 g of cis-endo-2-[(3,5-bistrifluoromethyl phenyl)-aminocarbonyl]-bicyclo-(2,2,1)-heptane-2carboxylic acid, the title compound was obtained in the same manner as in Example 7.

Melting point: 238°–239° C.
Elemental analysis: for $C_{17}H_{15}NO_3F_6$

|  | C | H | N |
|---|---|---|---|
| Calculated (%): | 51.65 | 3.83 | 3.54 |
| Found (%): | 51.87 | 3.81 | 3.56 |

EXAMPLE 12

Cis-2-[(3,5-bistrifluoromethyl phenyl)-aminocarbonyl]-4(5)-methyl-cyclohexane carboxylic acid Starting from 2.3 g of 3,5-bistrifluoromethyl aniline and 1.6 g of 4-methyl cyclohexane carboxylic acid, the title compound was obtained in the same manner as in Example 1.

Melting point: 174°–175° C.
Elemental analysis: for $C_{17}H_{17}NO_3F_6$

|  | C | H | N |
|---|---|---|---|
| Calculated (%): | 51.38 | 4.32 | 3.52 |
| Found (%): | 51.49 | 4.34 | 3.49 |

EXAMPLE 13

N-(3,5-bistrifluoromethyl phenyl)-cyclohexane-1,2-dicarboximide 7.3 g of the amide carboxylic acid made in Example 1 was dehydrated by heating to a temperature of 180° C. for two hours. The products were recrystallized from the solvent mixture (1:1) of iso-propyl ether and n-hexane to give 3.5 g of the title compound.

Melting point: 85°–87° C.
Elemental analysis: for $C_{16}H_{13}NO_2F_6$

|  | C | H | N |
|---|---|---|---|
| Calculated (%): | 52.60 | 3.59 | 3.83 |
| Found (%): | 52.63 | 3.62 | 3.83 |

EXAMPLE 14

N-(3,5-bistrifluoromethyl phenyl)-4-cyclohexene-1,2-dicarboximide

The title compound was obtained by the procedure similar to Example 13.

Melting point: 150°–152° C.
Elemental analysis: for $C_{16}H_{11}NO_2F_6$

|  | C | H | N |
|---|---|---|---|
| Calculated (%): | 52.89 | 3.05 | 3.85 |
| Found (%): | 53.03 | 3.13 | 3.83 |

EXAMPLES 15 TO 19

Hereinbelow will be illustrated a process for the production of the metal salts fallen within the present invention and their properties.

PRODUCTION PROCESS 10 m Mol of cis-2-[(3,5-bistrifluoromethyl phenyl)-aminocarbonyl]-cyclohexane carboxylic acid was dissolved in 100 ml of 0.1N NaOH/methanol solution. The solvent was evaporated off to dryness to give sodium cis-2-[(3,5-bistrifluoromethyl phenyl)-aminocarbonyl]-cyclohexane carboxylate [melting point: 259°–260° C. (decomposition)].

Similarly, starting from the corresponding amide carboxylic acid, the following compounds were obtained:

Sodium trans-2-[(3,5-bistrifluoromethyl phenyl)-aminocarbonyl]-cyclohexane carboxylate. Melting point: above 280° C.

Sodium cis-6-[(3,5-bistrifluoromethyl phenyl)-aminocarbonyl]-3-cyclohexane carboxylate. Melting point: 226°–227° C. (decomposition).

Sodium 2-[(3,5-bistrifluoromethyl phenyl)-aminocarbonyl]-1-cyclohexene carboxylate. Melting point: 125°–127° C.

Sodium cis-2-[(3,5-bistrifluoromethyl phenyl)-aminocarbonyl]-4(5)-methyl-cyclohexane carboxylate. Melting point: 165° C. (decomposition).

What is claimed is:

1. A carboxylic acid amide derivative represented by the formula (I):

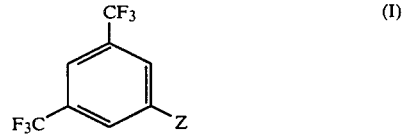  (I)

wherein Z represents a group of the formula:

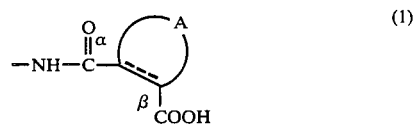  (1)

wherein A constitutes along with two carbon atoms respectively represented by α and β, a group of the formula:

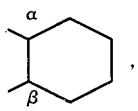, a group of the formula:

a group of the formula:

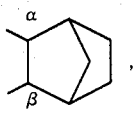

a group of the formula:

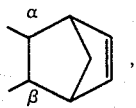

or a group of the formula:

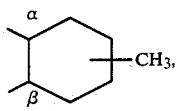

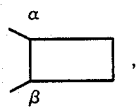

and ═══════ denotes a single bond or a double bond, or a pharmaceutically acceptable salt thereof.

2. The carboxylic acid amide as claimed in claim 1, wherein Z represents a group of the formula:

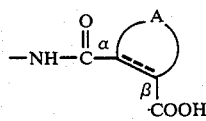

and A represents a group of the formula:

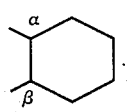

3. The carboxylic acid amide as claimed in claim 1, wherein Z represents a group of the formula:

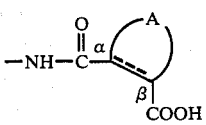

and A represents a group of the formula:

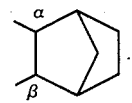

4. The carboxylic acid amide as claimed in claim 1, wherein Z represents a group of the formula:

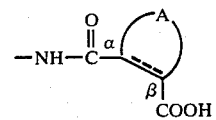

and A represents a group of the formula:

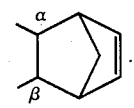

5. The carboxylic acid amide as claimed in claim 1, wherein Z represents a group of the formula:

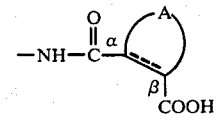

and A represents a group of the formula:

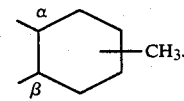

6. The carboxylic acid amide as claimed in claim 1, wherein Z represents a group of the formula:

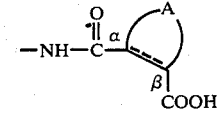

and A represents a group of the formula:

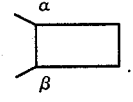

7. Cis-2-[(3,5-bistrifluoromethyl)-phenyl-aminocarbonyl]-cyclohexane carboxylic acid according to claim 1.

8. Trans-2-[(3,5-bistrifluoromethyl)-phenyl-aminocarbonyl]-cyclohexane carboxylic acid according to claim 1.

9. Cis-endo-3-[(3,5-bistrifluoromethyl-phenyl)-aminocarbonyl]-bicyclo-(2,2,1)-heptane-2-carboxylic acid according to claim 1.

10. Cis-2-[(3,5-bistrifluoromethyl-phenyl)-aminocarbonyl]-4(5)-methyl-cyclohexane carboxylic acid according to claim 1.

* * * * *